United States Patent [19]

Lucas, Sr.

[11] Patent Number: Plant 6,458

[45] Date of Patent: Dec. 13, 1988

[54] GRAPEVINE, "FLAMED GLOBE"

[76] Inventor: George A. Lucas, Sr., P.O. Box 520, Delano, Calif. 93216

[21] Appl. No.: 22,621

[22] Filed: Feb. 24, 1987

[51] Int. Cl.[4] ..... A01H 5/03

[52] U.S. Cl. ..... Plt./47

[58] Field of Search ..... Plt./47

*Primary Examiner*—Robert E. Bagwill

*Attorney, Agent, or Firm*—Worrel & Worrel

[57] ABSTRACT

The grapevine particularly characterized by its production of berries which are generally similar to those produced by the Emperor Grapevine (unpatented) but which is characterized as to novelty by producing grapes which are mature for commercial harvesting approximately September 1 through September 15 under the ecological conditions prevailing in the San Joaquin Valley of Central California.

1 Drawing Sheet

BACKGROUND OF THE INVENTION

The present invention relates to a new and distinct variety of grapevine to be known as the "Flamed Globe", and more particularly to a grapevine which is somewhat similar in physical characteristics to the Emperor Grapevine (unpatented) but from which it is distinguished by producing grapes which are ripe for commercial harvesting approximately from September 1 through September 15 at Delano, Calif. which is three to four weeks earlier than the Emperor Grapevine and which produces bunches of grapes having sizes, weights and color which is somewhat different than the Emperor Grapevine.

From a commercial standpoint, the relative times of ripening of various varieties of grapevines or other fruits are obviously extremely important. It has long been recognized as desirable to provide grapevines that bear fruit earlier than varieties that it most nearly resembles whereby the fruit can be brought to market when competition is at a minimum. In addition, if the ripening periods of various grapes can be spread over a longer period of time, savings and increased efficiency can be attained because the capital which is generally required to harvest and then transport the grapes which are harvested within a relatively short ripening period can be spread over a longer period of time resulting in lower costs of the final product and increasing the uniformity of production.

In a continuing effort to upgrade the quality of his grapevine, the applicant is constantly on the alert to locate any new varieties that may appear as a consequence of the random cross-pollination of grapevine having known desirable traits. The applicant, in this regard discovered within the cultivated area of his vineyard located at Avenue 16 and Road 184, east of the Kern-Friant Canal in Delano, Calif., in 1976 a randomly cross-pollinated grapevine of unknown parentage.

ORIGIN AND ASEXUAL REPRODUCTION OF THE NEW VARIETY

The new variety of grapevine was discovered by the inventor, in 1976, in his commercial vineyard located at Avenue 16 and Road 184 east of the Kern-Friant Canal in a test block of grapevines purchased from a previous owner. The vineyard is located in Delano, Calif. in the County of Kern.

The new variety of grapevine was discovered among a multiplicity of randomly cross-pollinated grapevines of unknown parentage. The new variety was asexually reproduced in 1979 by the inventor by removing softwood cuttings from the original grapevine and thereafter grafting them into Calmeria grapevines (unpatented) which were then located at the inventor's vineyard which is located at Avenue 16 and Road 176 near Delano, Calif. The grapevines produced from these softwood cuttings have been continuously observed by the inventor and have proven to be identical in characteristics with respect to those of the original grapevine.

SUMMARY OF THE NEW VARIETY

The new variety of grapevine is generally characterized by its bearing a reddish brown, substantially obovoid shaped berry that somewhat remotely resembles the variety Emperor (unpatented), but which matures several weeks earlier than the Emperor Grapevine and which bears fruit which ripens for commercial harvesting approximately September 1 through September 15, under the ecological conditions prevailing in the San Joaquin Valley of Central California. The new variety of grapevine is to be known as the "Flamed Globe".

BRIEF DESCRIPTION OF THE DRAWINGS

The accompanying drawing is a color photograph displaying two bunches of mature grapes of the new variety together with representative leaves showing their dorsal and ventral coloration, and several grapes of the subject variety halved in the axial plane and transverse to the axial plane to illustrate the flesh coloration thereof.

DETAILED DESCRIPTION

Referring more particularly to the pomological details of this new and distinct variety of grapevine the following has been observed under the ecological conditions prevailing at the designated vineyard in Delano, Calif. The color code identifications are by reference to the Inter-Society Color Council—National Bureau of Standards; common descriptive color names are also used occasionally.

VINE

Generally:

*Size.*—Large, as controlled by pruning techniques.

*Growth.*—Vigorous.

*Productivity.*—Heavy; regular; a typical young vine produces 50 clusters of grapes per vine.

Canes:

*Generally.*—Stout.

*Joints.*—Spacing — average, approximately 3–4 inches, (76.2 through 101.6 mm.).

*Tendrils.*—Thickness — average. Length — medium. Numbers — average. Size — medium.

*Color.*—Light green, (120 m. Y G.).

Flowers:

*Numbers.*—Abundant.

*Date of bloom.*—Generally — 2 weeks; approximately May 1 to 15 at Delano, Calif.

*Blossom color.*—Yellowish, the color of the blossom is not distinctive.

*Reproductive organs.*—Stamens — size — medium. Filaments — size — average. Pollen production — normal.

*Peduncle.*—Size — average, approximately 8 inches in length, (203.2 mm.).

LEAVES

Size:

*Generally.*—Average in overall appearance.

*Numbers.*—Average.

*Texture.*—Dorsal surface — glabrous.

*Form.*—Cuneiform.

*Terminal body.*—Acute.

*Petiolar sinus.*—Form — sagitate.

*Petiolar sinus.*—Depth — deep.

*Lateral sinus.*—Generally — average in depth, although some leaves may occasionally have a lateral sinus which is shallow or very shallow in depth.

*Lateral sinus.*—Width — average.

*Marginal form.*—Generally — palmately lobed with teeth of average width and depth. Teeth — form — generally serrate.

*Leaf arrangement.*—Generally alternate.

*Leaf venation.*—Generally — net, palmate.

*Color — dorsal surface — mature leaves.*—Dark green, (126. d 01 G).

*Color — ventral surface — mature leaves.*—Light green, (118. deep Y G).

*Color — petiole — mature leaves.*—Green, (119. 1. Y G).

*Color — dorsal surface — young leaves.*—Light green (120 m. Y G).

*Color — ventral surface — young leaves.*—Light green, (120 m. Y G).

*Color — petiole — young leaves.*—Variable; green and occasionally red, (39, gy. r O).

FRUIT

Maturity when described: Ripe for commercial harvesting — September 1 through September 15 under the ecological conditions prevailing in the San Joaquin Valley of Central California.

Keeping quality: Noteworthy.

Shipping quality: Excellent.

Eating quality: Excellent.

Cluster:

*Size.*—Average.

*Width.*—Medium.

*Shape.*—Oblong.

Clusters ripen: Evenly.

Berry:

*Size.*—Generally — large.

*Diameter.*—Transverse to axial plane — approximately $\frac{7}{8}$ of an inch, (22.225 mm.).

*Axial diameter.*—Approximately 1 inch, (25.4 mm.).

*Shape.*—Generally — obovoid.

*Color.*—A reddish brown, (43. m. Br.).

Skin:

*Generally.*—Tight.

Texture: Hard.

Flesh:

*Color.*—Translucent, although occasionally mature berries display the same color as the skin.

Seeds:

*Generally.*—Present.

*Number of seeds per berry.*—Generally — two.

Use: Fresh market.

Although the new variety of grapevine possesses described characteristics as a result of the growing conditions prevailing in the San Joaquin Valley of Central California, it is to be understood that variations of the usual magnitude incident to growing conditions, fertilization, pruning and pest control are to be expected.

Having thus described and illustrated my new variety of grapevine, I claim:

1. A new and distinct variety of grapevine to be designated varietally as the Flamed Globe substantially as illustrated and described which is characterized principally as to novelty by its production of grapes which are mature for commercial harvesting approximately September 1 through September 15 under the ecological conditions prevailing in the San Joaquin Valley of Central California, said grapes maturing several weeks earlier than the Emperor Grapevine (unpatented) with which it most closely resembles but from which it is distinguished by producing berries which have a reddish brown color and which further have leaves which have a sagitate petiolar sinus and serrate marginal edge.

* * * * *

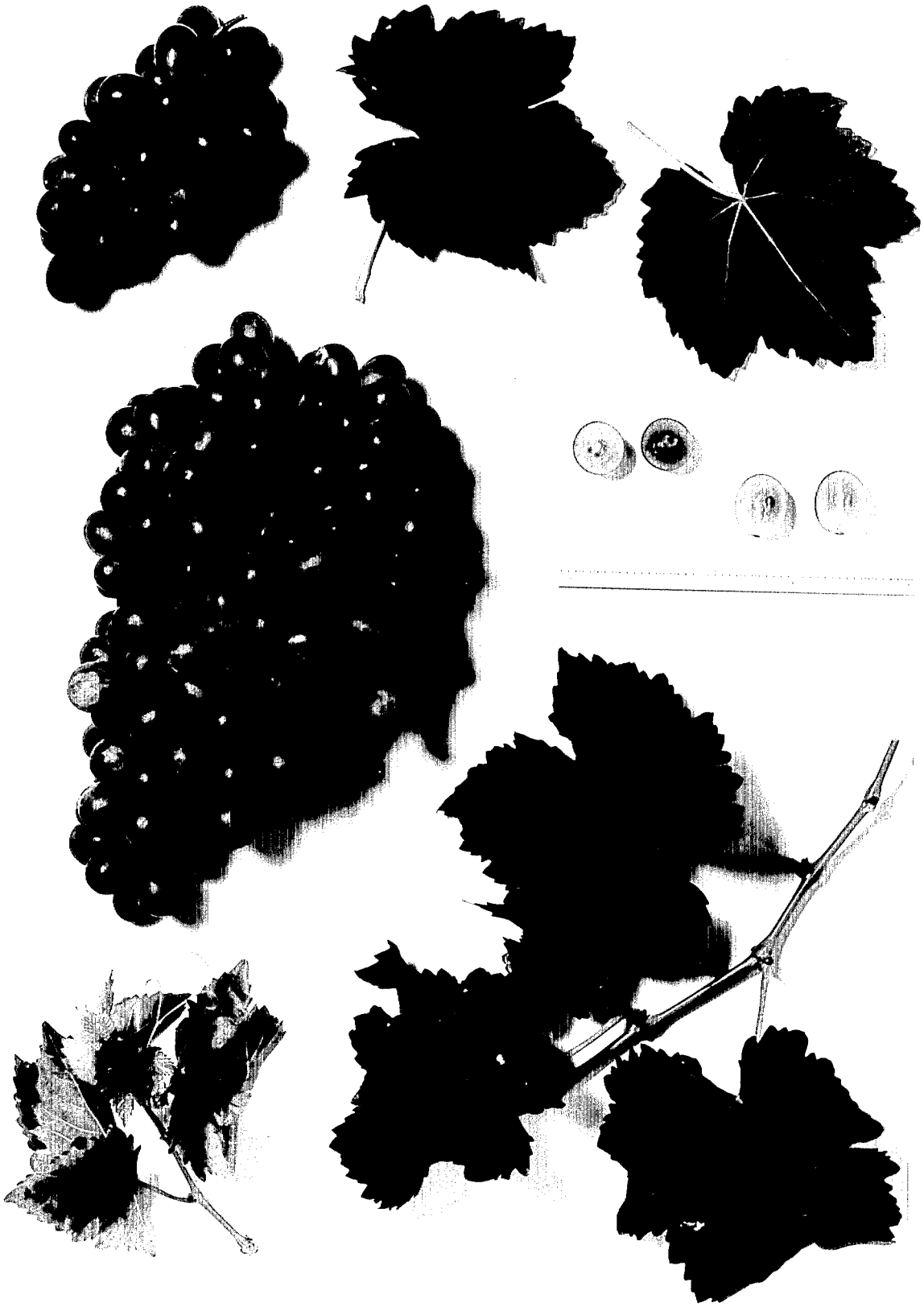

UNITED STATES PATENT AND TRADEMARK OFFICE

CERTIFICATE OF CORRECTION

PATENT NO. : PP 06458

DATED : December 13, 1988

INVENTOR(S) : George A. Lucas

It is certified that error appears in the above-identified patent and that said Letters Patent is hereby corrected as shown below:

Column 3, Line 30, delete "body" and substitute ---- lobe ----.

Signed and Sealed this

Eighteenth Day of April, 1989

*Attest:*

DONALD J. QUIGG

*Attesting Officer*

*Commissioner of Patents and Trademarks*